United States Patent
Datta et al.

(10) Patent No.: US 11,120,891 B2
(45) Date of Patent: Sep. 14, 2021

(54) METHOD FOR DETECTING A MINORITY GENOTYPE

(71) Applicant: Gen-Probe Incorporated, San Diego, CA (US)

(72) Inventors: Somalee Datta, Sunnyvale, CA (US); Brett Bowman, San Diego, CA (US); Xianqun Wang, San Marcos, CA (US); Mingjie Wang, Bloomington, IN (US)

(73) Assignee: GEN-PROBE INCORPORATED, San Diego, CA (US)

( * ) Notice: Subject to any disclaimer, the term of this patent is extended or adjusted under 35 U.S.C. 154(b) by 48 days.

(21) Appl. No.: 14/414,688

(22) PCT Filed: Jul. 11, 2013

(86) PCT No.: PCT/US2013/050095
§ 371 (c)(1),
(2) Date: Jan. 13, 2015

(87) PCT Pub. No.: WO2014/011892
PCT Pub. Date: Jan. 16, 2014

(65) Prior Publication Data
US 2015/0211079 A1    Jul. 30, 2015

Related U.S. Application Data

(60) Provisional application No. 61/671,298, filed on Jul. 13, 2012, provisional application No. 61/703,639, filed on Sep. 20, 2012.

(51) Int. Cl.
*G16B 40/00* (2019.01)
*G16B 20/00* (2019.01)
(Continued)

(52) U.S. Cl.
CPC .......... *G16B 40/00* (2019.02); *C12Q 1/6809* (2013.01); *G16B 20/00* (2019.02); *G16B 20/20* (2019.02);
(Continued)

(58) Field of Classification Search
None
See application file for complete search history.

(56) References Cited

PUBLICATIONS

GP Wang, SA Sherrill-Mix, KM Chang, C Quince, FD Bushman. Hepatitis C Virus Transmission Bottlenecks Analyzed by Deep Sequencing. Journal of Virology, Jun. 2010, vol. 84, No. 12, p. 6218-6228.*

(Continued)

*Primary Examiner* — Olivia M. Wise
(74) *Attorney, Agent, or Firm* — Alston & Bird LLP; Jeff Landes

(57) ABSTRACT

Disclosed are methods for detecting a minority genotype of a target nucleic acid. The disclosed method generally includes the steps of (a) deep sequencing at least a portion of the target nucleic acid; (b) using the deep sequencing results of (a) to detect the presence of variant nucleobases at one or more nucleotide reference positions within the target nucleic acid; (c) using the variant detection results generated in step (b) to perform a statistical analysis of whether the variants are significant; and (d) using the variant detection and variant significance results generated in steps (b) and (c) to perform a statistical analysis of whether a subset of sequences together exhibit a common set of significant variants.

12 Claims, 1 Drawing Sheet

(51) Int. Cl.
  *G16B 20/20*  (2019.01)
  *C12Q 1/6809*  (2018.01)
(52) U.S. Cl.
  CPC . *C12Q 2600/106* (2013.01); *C12Q 2600/156* (2013.01); *C12Q 2600/16* (2013.01)

(56) References Cited

PUBLICATIONS

SF Chen, J Goodman. An Empirical Study of Smoothing Techniques for Language Modeling. Proceedings of the 34th annual meeting on Association for Computational Linguistics Jun. 1996, pp. 310-318.*
WS Noble. How does multiple testing correction work? Nat Biotechnology 2009, vol. 27, No. 12, p. 1135-1137.*
AK Jain. Data clustering: 50 years beyond k-means. Pattern Recognition Letters 2010, vol. 31, p. 651-666.*
C Meldrum, MA Doyle, RW Tothill. Next-Generation Sequencing for Cancer Diagnostics: A practical perspective. Clin Biochem Rev, Nov. 2011, vol. 32, p. 177-195.*
H Li. A statistical framework for SNP calling, mutation discovery, association mapping and population genetical parameter estimation from sequencing data. Bioinformatics 2011, vol. 27, No. 21, p. 2987-2993.*
Rodriguez-Frias et al. Ultra-Deep Pyrosequencing Detects Conserved Genomic Sites and Quantifies linkage of drug-resistant amino acid chagnes in the hepatitis B virus genome. PLoS One, May 2012, vol. 7, Issue 5, e37874.*
T Huang, K Tu, Y Shyr, CC Wei, L Xie, YX Li. The prediction of interferon treatment effects based on time series microarray gene expression profiles. Journal of Translational Medicine Aug. 2008, vol. 6, No. 44, pp. 1-9.*
L. Barzon, E Lavezzo, V Militello, S Toppo, G Palu. Applications of Next-Generation Sequencing Technologies to Diagnostic Virology. Int. J. Mol. Sci. 2011, vol. 12, p. 7861-7884.*
C Hedskog, M Mild, J Jernberg, E Sherwood, G Bratt, T Leitner, J Lundeberg, B Andersson, J Albert. Dynamics of HIV-1 Quasispecies during Antiviral Treatment Dissected Using Ultra-Deep Pyrosequencing. PLoS One, Jul. 2010, vol. 5, Issue 7, e11345, p. 1-14.*
T Le, J Chiarella, BB Simen, B Hanczaruk, M Egholm, ML Landry, K Dieckhaus, MI Rosen, MJ Kozal. Low-Abundance HIV Drug-Resistant Viral Variants in Treatment-Experienced Persons Correlate with Historical Antiretroviral Use, PLoS One, Jun. 2009, vol. 4, Issue 6, e6079, p. 1-8.*
APO Patent Examination Report No. 1, Australian Patent Application No. 2013205087, dated Jan. 21, 2015.
Verbinnen et al., "Tracking the Evolution of Multiple In Vitro Hepatitis C Virus Replicon Variants under Protease Inhibitor Selection Pressure by 454 Deep Sequencing," J Virol., 2010, 84(21):11124-33, American Society for Microbiology, USA.
Gerlinger et al., "Intratumor Heterogeneity and Branched Evolution Revealed by Multiregion Sequencing," N Engl J Med, 2012, 366(10):883-92, Melbourn, Royston, Herts: Massachusetts Medical Society.
Stransky et al., "The Mutational Landscape of Head and Neck Squamous Cell Carcinoma," Science, 2011, 333(6046):1157-60, American Assn. for the Advancement of Science.
Travers et al., "A Flexible and Efficient Template Format for Circular Consensus Sequencing and SNP Detection," 2010, 38(15):e159, London, Information Retrieval ltd.
APO Notice of Acceptance, Australian Patent Application No. 2013205087, dated Feb. 19, 2016.
EPO Communication pursuant to Article 94(3) EPC, European Application No. 13740457.0, dated Mar. 24, 2016.
Bansal et al., "A statistical method for the detection of variants from next-generation resequencing of DNA pools," 2010, Bioinformatics, vol. 26, No. 12, pp. i318-i324, Oxford University Press.
Wu et al., "Rare-Variant Association Testing for Sequencing Data with the Sequence Kernel Association Test," 2011, Am J Hum Genet, vol. 89, No. 1, pp. 82-93, American Society of Human Genetics, USA.
PCT International Preliminary Report on Patentability, International Application No. PCT/US2013/050095, dated Jan. 13, 2015.
PCT Written Opinion, International Application No. PCT/US2013/050095, dated Sep. 18, 2013.
PCT Search Report, International Application No. PCT/US2013/050095, dated Sep. 18, 2013.
EP 13740457.0 Communication pursuant to Article 94(3) EPC dated Feb. 20, 2017.
EP 18157235 Extended European Search Report dated Apr. 30, 2018.
Ding, et al., "Clonal evolution in relapsed acute myeloid leukaemia revealed by whole-genome sequencing," Nature, vol. 481, pp. 506-510, (Jan. 26, 2012).
Forshew, et al., "Noninvasive Identification and Monitoring of Cancer Mutations by Targeted Deep Sequencing of Plasma DNA," www.ScienceTranslationalMedicine.org, vol. 4, Issue 136, 136ra68, May 30, 2012.
Stansky, et al., "The Mutational Landscape of Head and Neck Squamous Cell Carcinoma," Science, published Jul. 28, 2011 on Science Express, doi:10.1126/science.1208130, (2011).
Zhou, et al., "Improving Sequence-Based Genotype Calls with Linkage Disequilibrium and Pedigree Information," The Annals of Applied Statistics, vol. 6, No. 2, 457-475, (2012).

* cited by examiner

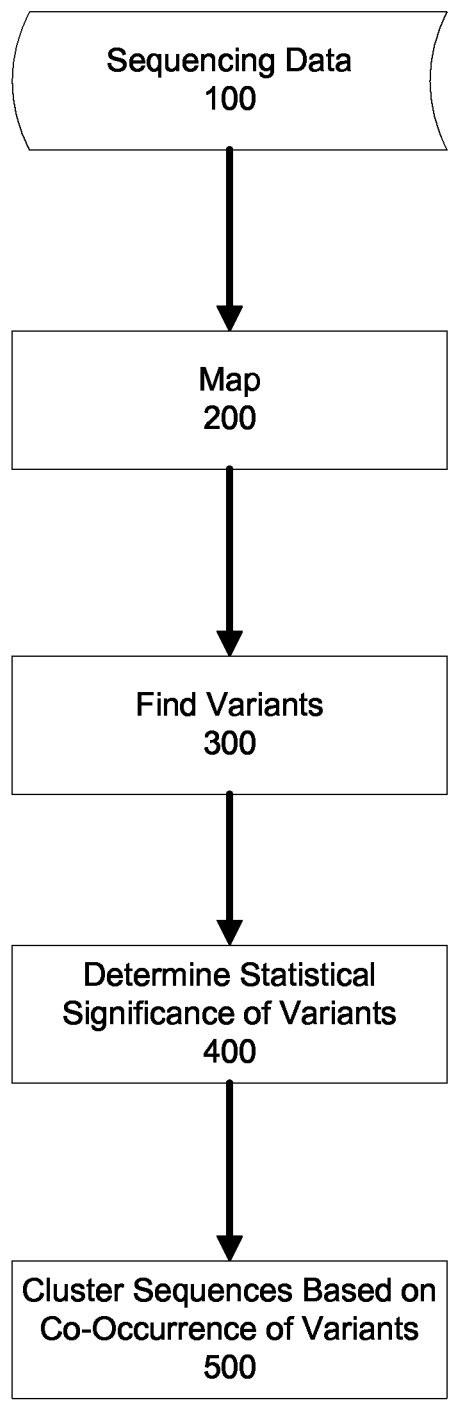

METHOD FOR DETECTING A MINORITY GENOTYPE

PRIORITY

This application is a U.S. national phase application of International Application No. PCT/US2013/050095, filed on Jul. 11, 2013, which claims priority to the following United States Provisional Applications: U.S. Provisional App. No. 61/671,298 filed 13 Jul. 2012; and U.S. Provisional App. No. 61/703,639 filed 20 Sep. 2012. The entire contents of each of these applications are incorporated herein by reference.

BACKGROUND OF THE INVENTION

Genotype variants can influence biological responses during the progression and/or treatment of various diseases or disorders, including, e.g., cancer, autoimmune disorders, and infectious disease. Indeed, disease subtypes defined by differences in genotype (e.g., viral or mammalian genotype) can be predictive of clinical outcomes such as, e.g., disease recurrence, survival, disease-free survival, and the like.

For example, hepatitis C virus (HCV) is an RNA virus that is the causative agent of chronic and acute hepatitis in about 170-200 million persons worldwide. HCV mutates rapidly as it replicates and the process of constant mutation helps the virus escape the body's immune response. The virus exhibits extreme genetic heterogeneity and is generally classified as a viral quasispecies consisting of a dominant majority species and a cloud of genetically distinct minority species. It is known that major HCV genotypes are indicative of disease prognosis and can influence viral response to drugs. For example, some studies suggest that infections of type 1, in particular type 1b, may be associated with more severe disease and earlier recurrence (Zein et al., *Liver Transplant. Surg.* 1:354-357, 1995; Gordon et al., *Transplantation* 63:1419-1423, 1997). Certain studies have also indicated that genotypes other than type 1 may respond more favorably to various treatments, e.g. interferon (McHutchison et al., *N. Engl. J. Med.,* 339:1485-1492, 1998).

There is now mounting evidence that viral subtypes, where each sub-type is typically composed of many different quasispecies, may also play a role. For example, differences between HCV subtype 1a and 1b include different efficacies of antiviral drugs and different resistance profiles to such drugs. (Chevaliez et al., *PLoS ONE* 4:e8209, 2009.) Several HCV inhibitors appear to have selective activity against different HCV genotype 1 subtypes, both in vitro and in vivo. (Id.) Differences have been observed, e.g., in vitro with NS3/4A protease inhibitors, non-nucleoside inhibitors of HCV RdRp, and NS5A inhibitors (Erhardt et al., *Antivir. Ther.* 14:23-32, 2009; Jiang et al., *J. Hepatol.* 50 (suppl. 1):S6, 2009; Liang et al., *Gastroenterology* 135:1710-1718, 2008; Nettles et al., *Hepatology* 48 (suppl. 1):1025A, 2008; Thompson et al., *J. Hepatol.* 50 (suppl. 1):S37, 2009). Accordingly, correct identification of HCV subtypes 1a and 1b is important in clinical trials assessing new HCV drugs in order to correctly stratify and interpret efficacy and resistance data. In addition, such genotype identification is likely to become increasingly important in clinical practice to select HCV inhibitor treatment according to HCV genotype 1 subtype. (See Chevaliez et al., supra.)

Another example is low frequency mutation in cancer patients. Cancer tumors typically show significant intratumor heterogeneity. In these circumstances, it is important to be able to identify the different co-existing clonal sub-types. The prevalence of sub-types change during the course of treatment and recurrence (Clonal evolution in relapsed acute myeloid leukaemia revealed by whole-genome sequencing, *Nature* 2012, doi:10.1038/nature10738).

The identification of minority genotypes, including rare or as yet unknown minority genotypes, would further facilitate, e.g., characterizing the relationship between genotype variants and biological responses, including clinical outcomes and interpretation of efficacy and resistance data. Accordingly, there remains a need for methods of efficiently detecting minority genotypes. The present invention meets these and other needs.

SUMMARY OF THE INVENTION

In one aspect, the present invention provides a method for detecting a minority genotype of a target nucleic acid. The method generally includes (a) deep sequencing at least a portion of the target nucleic acid; (b) using the deep sequencing results of (a) to detect the presence of variant nucleobases at one or more nucleotide reference positions within the target nucleic acid; (c) using the variant detection results generated in step (b) to perform a statistical analysis of whether the variants are significant; and (d) using the variant detection and variant significance results generated in steps (b) and (c) to perform a statistical analysis of whether a subset of sequences together exhibit a common set of significant variants (i.e., whether a set of significant variants are statistically likely to co-occur). If a subset of sequences together exhibit a common set of significant variants, a minority genotype of the target nucleic acid is detected. Suitable deep sequencing methods for use in accordance with the present invention include single molecule real time (SMRT™) sequencing, Ion Torrent™ ion semi conductor sequencing, MiSeq™ sequencing, and HiSeq™ bridge polymerase chain reaction sequencing. In some embodiments, the method further includes amplifying one or more regions of the target nucleic acid prior to step (a), and the deep sequencing comprises sequencing the one or more amplified regions.

In some embodiments, the variant detection and variant significance is based on a parametric model. Alternatively, the variant detection and variant significance is based on a non-parametric model. In certain variations, the variant detection and variant significance is based on a Bayesian model.

In some embodiments, computation of variant significance comprises additive smoothing (e.g., Laplace or Lidstone smoothing) or a derivative thereof. In other embodiments, computation of variant significance includes correction by a false discovery rate minimization method. Particularly suitable false discovery rate minimization methods include Bonferroni correction, Benjamini and Hochberg correction, or a derivative thereof.

In certain variations, the statistical analysis of step (d) (using the variant detection and variant significance results generated in steps (b) and (c) to perform a statistical analysis of whether a subset of sequences together exhibit a common set of significant variants) comprises a clustering method. Particularly suitable clustering methods include non-negative matrix factorization, k-means, singular value decomposition, principal component analysis, and derivatives thereof.

In some embodiments, the target nucleic acid is a viral nucleic acid, such as, for example, a hepatitis C virus (HCV) nucleic acid (e.g., HCV type 1a or type 1b). In more specific variations, the target region of the HCV target nucleic acid includes at least one of the NS3, NS4, and NS5 regions from HCV.

The target nucleic acid can be from a sample obtained from a patient suffering or at risk of a disease or disorder. In some such variations, the method further includes determining a treatment regime for the patient based on the detection of the minority genotype. In particular embodiments, the patient is infected with HCV.

In other embodiments, the minority genotype is detected in a plurality of samples from patients suffering from a disease or disorder, where the patients are receiving a predetermined treatment regime for the disease or disorder. In some such variations, the method further includes (i) monitoring the patients to obtain efficacy and/or resistance data for the treatment regime and (ii) determining the presence or absence of a correlation between the detected minority genotype and the efficacy and/or resistance data. In particular embodiments, the patients are infected with HCV.

In certain variations, the target nucleic acid is obtained from a plurality of samples from each of one or more patients suffering from a disease or disorder, where the one or more patients are receiving a predetermined treatment regime for the disease or disorder. In one aspect, at least two of the samples (e.g., at least three or at least four of the samples) are from two different patients, wherein each patient is receiving a different treatment condition (e.g., sample 1 from a patient receiving placebo and sample 2 from a patient receiving a drug treatment; or sample 1 from a patient receiving drug treatment A and sample 2 from a patient receiving drug treatment B). In another aspect, at least two of the samples (e.g., at least three or at least four of the samples) from each patient each corresponds to a different time point during the course of the treatment regime, where steps (a)-(d) as discussed above are performed with respect to the target nucleic acid from each of the at least two samples. Typically, at least one of the samples corresponding to a different time point corresponds to a time point before the treatment regime starts, and at least one of the samples corresponding to a different time point corresponds to a time point after the treatment regime starts. In some variations, at least two of the samples corresponding to a different time point each corresponds to a different time point after the treatment regime starts. For example, where at least three of the samples from each patient each corresponds to a different time point during the course of the treatment regime, at least one of the samples corresponding to a different time point may correspond to a time point before the treatment regime starts, and at least two of the samples corresponding to different time points may each correspond to a different time point after the treatment regime starts. In certain embodiments, the variation detection results of step (b) include a determination of the frequency for each variant and/or the variant significance results of step (c) include a significance value (e.g., a Poisson p-value) assigned to each variant, and the method further includes (e) for each of one or more variants within the common set of significant variants determined in step (d), comparing the variant frequencies and/or variant significance values for the samples corresponding to different time points to determine whether the variant exhibits different frequencies and/or significance values during the course of the treatment regime ("differential variant"). Where a plurality of minority genotypes are detected within the samples corresponding to different time points, the method may further include (e) optionally selecting a subset of the plurality of minority genotypes (e.g., based on the statistical analysis performed in step (d)), and (f) for each of one or more variants within the common set of significant variants determined in step (d) for each minority genotype within the plurality or optional subset thereof, comparing the variant frequencies and/or variant significance values for the samples corresponding to different time points to determine whether the variant is a differential variant. If a plurality of differential variants are identified in step (f), the method may further include (g) selecting at least a subset of the plurality of differential variants, and (h) performing two-way hierarchical clustering on (1) the frequencies and/or significance values of the differential variants within the plurality or subset thereof and (2) the samples containing the target nucleic acid in which differential variants were detected, each sample corresponding to a time point during the course of the treatment regime. In some such embodiments, a correlation between at least one differential variant and the course of the treatment regime is determined based on results from the two-way hierarchical clustering. The method may further include monitoring the one or more patients to obtain efficacy and/or resistance data for the treatment regime, and determining a correlation between at least one differential variant and the efficacy and/or resistance data. In some embodiments, the method further includes confirming at least one differential variant by a technology such as Sanger sequencing.

In other embodiments, the target nucleic acid is obtained from a plurality of samples from each of one or more patients suffering from a disease or disorder, at least two of the samples (e.g., at least three or at least four of the samples) from each patient each corresponds to a different time point during the course of disease or disorder progression, and steps (a)-(d) as discussed above are performed with respect to the target nucleic acid from each of the at least two samples. In certain embodiments, the variation detection results of step (b) include a determination of the frequency for each variant and/or the variant significance results of step (c) include a significance value (e.g., a Poisson p-value) assigned to each variant, and the method further includes (e) for each of one or more variants within the common set of significant variants determined in step (d), comparing the variant frequencies and/or variant significance values for the samples corresponding to different time points to determine whether the variant exhibits different frequencies and/or significance values during the disease or disorder progression ("differential variant"). Where a plurality of minority genotypes are detected within the samples corresponding to different time points, the method may further include (e) optionally selecting a subset of the plurality of minority genotypes (e.g., based on the statistical analysis performed in step (d)), and (f) for each of one or more variants within the common set of significant variants determined in step (d) for each minority genotype within the plurality or optional subset thereof, comparing the variant frequencies and/or variant significance values for the samples corresponding to different time points to determine whether the variant is a differential variant. The method may also include determining a correlation between at least one differential variant and the disease or disorder progression. If a plurality of differential variants are identified in step (f), the method may further include (g) selecting at least a subset of the plurality of differential variants, and (h) performing two-way hierarchical clustering on (1) the frequencies and/or significance values of the differential variants within the plurality or subset thereof and (2) the samples containing the target nucleic acid in which differential variants were detected, each sample corresponding to a time point during the disease or disorder progression. In some such embodiments, a correlation between at least one differential variant and the disease or disorder progression is determined based on results from the two-way hierarchical clustering. In some embodiments, the method further includes confirming at least one differential variant by a technology such as Sanger sequencing.

Typically, in a method as set forth above in which the target nucleic acid is obtained from a patient suffering from a disease or disorder, the disease or disorder is characterized by heterogeneity in one or more disease-related genes and the target nucleic acid corresponds to one or more such genes. For example, the disease or disorder may be (i) an infectious disease associated with an infectious agent characterized by genetic heterogeneity or (ii) a cancer characterized by intra-tumor genetic heterogeneity. In some embodiments in which the disease or disorder is the infectious disease, the infectious agent is a virus and the target nucleic acid is a viral nucleic acid. In specific variations, the infectious agent is hepatitis C virus (HCV) and the target nucleic acid is an HCV nucleic such as, e.g., an HCV target nucleic acid containing a target region comprising at least one of the NS3, NS4, and NS5 regions.

These and other aspects of the invention will become evident upon reference to the following detailed description of the invention and the attached drawings.

Definitions

Unless defined otherwise, all technical and scientific terms used herein have the same meaning as commonly understood by one of ordinary skill in the art pertinent to the methods and compositions described. Reference to a technology by a company or trade name herein includes reference to the corresponding generic technology, unless otherwise indicated by context. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" includes any specimen that may contain a target nucleic acid. Samples include "biological samples," which include any tissue or material derived from a living or dead human that may a target nucleic acid, including, e.g., peripheral blood, plasma, serum, lymph node, gastrointestinal tissue (e.g., liver), vaginal swab samples, cervical brush samples, respiratory tissue or exudates such as bronchoscopy, bronchioalveolar lavage (BAL) or lung biopsy, sputum, saliva, feces, urine, semen, or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *BioTechniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

A "nucleotide" as used herein is a subunit of a nucleic acid consisting of a phosphate group, a 5-carbon sugar, and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide" unit as used herein (e.g., a non-nucleotide linker) is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a target sequence to be sequenced and analyzed according to the methods described herein. Target nucleic acids may be DNA or RNA as described herein, and may be either single-stranded or double-stranded. The target nucleic acid may include other sequences besides the target sequence, which may not be sequenced or analyzed.

By "isolated" it is meant that a biological constituent (e.g., a sample containing a target nucleic acid) is taken from its natural milieu, but the term does not connote any degree of purification.

The term "region," as used herein, refers to a portion of a nucleic acid wherein said portion is smaller than the entire nucleic acid. For example, when the nucleic acid is a target nucleic acid, the term "region" may be used to refer to a smaller area of the nucleic acid, wherein the smaller area is sequenced and analyzed according to the present invention or targeted by one or more oligonucleotides (e.g., by an amplification oligomer or capture probe oligomer).

In the context of nucleic acid amplification, the term "target region" as used herein refers to a particular region of the target nucleic acid that is to be amplified. The "target region" includes the complexing sequences to which oligonucleotides (e.g., priming oligonucleotides and/or promoter oligonucleotides) complex during an amplification processes (e.g., PCR, TMA). Where the target nucleic acid is originally single-stranded, the term "target region" will also refer to the sequence complementary to the "target region" as present in the target nucleic acid. Where the target nucleic acid is originally double-stranded, the term "target sequence" refers to both the sense (+) and antisense (−) strands.

As used herein, the terms "variant nucleobase" or "variant nucleotide" are synonymous and generally defined as a difference from a baseline reference nucleotide sequence or as a difference found between a subset of nucleic acids of particular type. For example, in the context of HCV nucleic acids, a "variant nucleobase" or "variant nucleotide" is generally defined as a difference from a baseline reference HCV nucleotide sequence or as a difference found between a subset of HCV nucleic acids of particular type (e.g., type 1) or subtype (e.g., 1a or 1b).

The term "deep sequencing," as used herein, refers to nucleic acid sequencing to a depth that allows each base to be read hundreds of times, typically at least about 500 times, more typically at least about 1000 times, and even more typically at least about 1500 times.

The interchangeable terms "oligomer," "oligo," and "oligonucleotide" refer to a polynucleotide having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to capture a target nucleic acid if it is capable of hybridizing to a target sequence in a target nucleic acid and further joins to a binding partner on an immobilized probe to capture the target nucleic acid to a support.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider." Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), reverse transcription polymerase chain reaction (RT-PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see, e.g., U.S. Pat. No. 4,786,600, incorporated by reference herein). LCR amplification uses four or more different oligonucleotides to amplify a target and its complementary strand by using multiple cycles of hybridization, ligation, and denaturation (see, e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein).

"Polymerase chain reaction" (PCR) uses a DNA polymerase, pairs of primers, and thermal cycling to synthesize multiple copies of two complementary strands of dsDNA or from a cDNA (see, e.g., U.S. Pat. Nos. 4,683,195; 4,683,202; and 4,800,159; each incorporated by reference herein). Generally, this process for amplifying a target region includes introducing an excess of at least two oligonucleotide primers (forward and reverse) to a mixture containing the desired target nucleic acid, followed by a precise sequence of thermal cycling in the presence of a DNA polymerase. To effect amplification, the mixture is denatured and the primers then annealed to their respective target sequences within complementary strands of the target nucleic acid. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The amplified segments created by the PCR process itself are, themselves, efficient templates for subsequent PCR amplifications. "Reverse transcription polymerase chain reaction" (RT-PCR) is a variant of PCR in which an RNA strand is reverse transcribed into its DNA complement (cDNA) using a reverse transcriptase, and the resulting cDNA is amplified using PCR.

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. Variations of transcription-associated amplification are well-known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein).

The term "amplicon" or the term "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons may also comprise non-target specific sequences if it is generated by an amplification oligomer member comprising a target-specific sequence and a non-target-specific sequence (such as, e.g., a promoter primer). Amplicons can be double stranded or single stranded and can include DNA, RNA or both.

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

"Sample preparation" refers to any steps or method that treats a sample for subsequent sequencing and analysis of a target nucleic acid present in the sample according the methods described herein, including, e.g., treatment of the sample for subsequent amplification of a nucleic acid target region prior to sequencing. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

The term "patient" or "subject," in the context of an individual having a disease or disorder and treatment thereof, includes mammals such as, for example, humans and other primates.

The term "treatment regime," in the context of treatment of a disease or disorder, refers to a combination of (i) amount(s) of one or more agents being administered to a patient and (ii) dosage frequency for each agent being administered.

BRIEF DESCRIPTION OF THE DRAWINGS

FIG. 1 is a block flow diagram illustrating a representative embodiment of a method for detecting a minority genotype.

DETAILED DESCRIPTION OF THE INVENTION

The present invention provides a method for detecting a minority (e.g., rare) genotype of a target nucleic acid. The method generally includes (1) the identification of variants and (2) linkage analysis of co-occurring variants to enable grouping or clustering sub-types within the larger population. The target nucleic acid may be, e.g., associated with a disease or disorder or a patient's potential response to one or more treatments for such disease or disorder, including, for example, infectious disease (e.g., HCV), cancer, or immune disorders such as, for example, autoimmune disease. The identification of minority genotypes according to the methods provided herein may in turn be useful for correlating one or more biological responses to the identified minority genotype. Particularly in the context of a disease or disorder, such identification may in turn be useful for, e.g., stratifying and interpreting efficacy and resistance data during clinical testing of a drug or for tailoring treatment schedules with one or more drugs according to a particular genotype for the target nucleic acid associated with the disease.

The method according to the present invention generally includes the following steps: (a) deep sequencing at least a portion of the target nucleic acid; (b) using the deep sequencing results of (a) to detect the presence of variant nucleobases at one or more nucleotide reference positions within the target nucleic acid; (c) using the variant detection results generated in step (b) to perform a statistical analysis of whether the variants are significant; and (d) using the variant detection and variant significance results generated in steps (b) and (c) to perform a statistical analysis of whether a subset of sequences together exhibit a common set of significant variants (i.e., whether a set of significant variants are statistically likely to co-occur). If a subset of sequences together exhibit a common set of significant variants, a minority genotype of the target nucleic acid is detected.

Using the method of the present invention, a minority genotype can be detected down to at least about 1% (1 variant nucleic acid in the presence of 100 wild-type nucleic acids). In certain embodiments, a minority genotype detected in accordance with the present invention represents a variant nucleic acid that is present at a frequency, within a representative population of corresponding nucleic acids, from at least about 1% to about 45%, from at least about 1% to about 40%, from at least about 1% to about 35%, from at least about 1% to about 30%, from at least about 1% to about 25%, from at least about 1% to about 20%, from at least about 1% to about 15%, from at least about 1% to about 10%, from at least about 1% to about 5%, from at least about 1% to about 4%, from at least about 1% to about 3%, or from at least about 1% to about 2%.

FIG. 1 illustrates a representative embodiment of the present method. Referring to FIG. 1 at 100, a target nucleic acid is deep sequenced. The sequencing data can be obtained, for example, from any of the next generation sequencing platforms, including but not limited to Pacific Biosciences RS ("PacBio RS"; single molecule real-time, or SMRT™, sequencing), Ion Torrent™ ion semi conductor personal genome machine (PGM), Illumina HiSeq™, and Illumina MiSeq™ bridge polymerase chain reaction sequencing. Typically, the sequencing data is in a FASTQ formatted file, where each sequence has an ID, a string of letters of length n representing the nucleotide sequence, and a string of quality values (typically ascii characters) representing length n that prescribes a quality or confidence score to the particular nucleotide call. In a particular embodiment, the sequencing data is FASTQ formatted and generated using SMRT™ sequencing.

Referring to FIG. 1 at 200, the sequencing data is aligned to a reference sequence of the region of interest. This could be an entire genome, a subset of the genome or, more specifically, a targeted region of the genome. The alignment method typically depends on the sequencing platform utilized to generate the sequencing data. Typically, software such as BWA (Li and Durbin, *Bioinformatics* 25:1754-60, 2010), BWA-SW (Li and Durbin, *Bioinformatics* 26:589-595, 2010), or other suitable alignment (mapping) software is used. In a particular embodiment, PacBio RS sequences are aligned using BWA-SW software with parameters suitable for PacBio sequences. Output of this stage is typically a SAM formatted file (Li et al., *Bioinformatics* 25:2078-2079, 2009).

Referring to FIG. 1 at 300, the aligned reads are statistically pooled at one or more particular loci on the reference genome and evaluated to establish potential variations from the loci (see, e.g., Li, *Bioinformatics* 27:2987-2993, 2011). These variants are typically single nucleotide polymorphisms (SNPs), multi-nucleotide polymorphisms (MNPs), small insertions or deletions (e.g., indels), large indels, genetic re-arrangements such as fusions, and the like. In a particular embodiment, the relevant variants are SNPs. Optionally, coordinate transformations can be applied to convert the nucleotide sequences to their corresponding three letter codon representations. In a particular embodiment, variants are computed both in nucleotide and codon space.

Referring to FIG. 1 at 400, for variants thus found in step 300, the significance of variance is computed using any of various statistical approaches. Multiple approaches are suitable at this stage. For example, a parametric model, such as a model based on Poisson distribution, may be assumed and p-values computed. Alternatively, non-parametric approaches are also suitable. In certain variations, a Bayesian model is used to establish likelihood estimates. Optionally, additive smoothing, such as Laplace smoothing, is applied to make the model more consistent. Optionally, a false discovery rate correction method is applied. In a particular embodiment, the significance of nucleotide and codon variants are separately computed using a Poisson model. In this embodiment, the Poisson model parameters are typically derived separately. In some such embodiments, an additional Laplace smoothing is applied to smooth the means of the Poisson distribution and consequently the p-values. In a separate embodiment, the Bonforroni FDR correction is applied to the computed p-values. The p-values can be used to select the most significant variants observed in the sequences.

Referring to FIG. 1 at 500, cluster analysis is performed. Sequences are clustered based on co-occurrence of variants. The most significant p-values can be used to determine the "features" of the clustering analysis. Any of many clustering algorithms can be used, including, for example, k-means, Principal Component Analysis, Singular Value Decomposition, or Non-negative Matrix Factorization (NMF). In a particular embodiment, NMF is used to generate clusters. Output of NMF is a set of clusters where each cluster has a score, a membership which is a subset of variants. Also, sequence IDs for sequences that belong to each cluster, and the number of sequences belonging to each cluster, may be obtained. Based on the cluster analysis, one or more subset of sequences in which a set of significant variants co-occur may be identified, thereby identifying one or more minority genotypes of the target nucleic acid.

In some embodiments, the method for detecting a minority genotype further includes amplifying one or more regions of the target nucleic acid prior to the deep sequencing step, and the deep sequencing comprises sequencing the one or more amplified regions. Generally, amplifying one or more target regions includes the following steps: (1) contacting a sample containing or suspected of containing the target nucleic acid with at least two amplification oligomers for amplifying at least one target region of the target nucleic acid; and (2) performing at least one in vitro nucleic acid amplification reaction, wherein any target nucleic acid present in the sample is used as a template for generating at least one amplification product corresponding to the at least one target region.

In certain embodiments, the method further includes purifying the target nucleic acid from other components in a sample before the deep sequencing step, or before any amplification step prior to sequencing. Such purification may include methods of separating and/or concentrating target nucleic acid contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains the target nucleic acid and other sample components.

In some embodiments, a target nucleic is selectively separated from other sample components by hybridizing the target nucleic acid to a capture probe oligomer. In some variations, the capture probe oligomer comprises a target-hybridizing sequence configured to specifically hybridize to a target sequence within the target nucleic acid so as to form a target-sequence:capture-probe complex that is separated from sample components. In other variations, the capture probe oligomer uses a target-hybridizing sequence that includes randomized or non-randomized poly-GU, poly-GT, or poly U sequences to bind non-specifically to a target nucleic acid so as to form a target-sequence:capture-probe complex that is separated from sample components. In specific variations, the capture probe oligomer comprises a target-hybridizing sequence that includes a randomized poly-(k) sequence comprising G and T nucleotides or G and U nucleotides (e.g., a $(k)_{18}$ sequence), such as described, for example, in WIPO Publication No. 2008/016988, incorporated by reference herein.

In a preferred variation, the target capture binds the target:capture-probe complex to an immobilized probe to form a target:capture-probe immobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further includes a sequence or moiety that binds the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to the target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle.

In particular variations, the capture probe oligomer comprises a randomized poly-(k) nucleotide sequence (e.g., $(k)_{18}$) and a 3' tail portion, preferably a substantially homopolymeric tail of about 10 to 40 nt (e.g., $T_3A_{30}$).

Target capture typically occurs in a solution phase mixture that contains one or more capture probe oligomers that hybridize to the target nucleic acid under hybridizing conditions, usually at a temperature higher than the $T_m$ of the tail-sequence:immobilized-probe-sequence duplex. For embodiments comprising a capture probe tail, the target:capture-probe complex is captured by adjusting the hybridization conditions so that the capture probe tail hybridizes to the immobilized probe, and the entire complex on the solid support is then separated from other sample components. The support with the attached immobilized-probe:capture-probe:target may be washed one or more times to further remove other sample components. Preferred embodiments use a particulate solid support, such as paramagnetic beads, so that particles with the attached target:capture-probe:immobilized-probe complex may be suspended in a washing solution and retrieved from the washing solution, preferably by using magnetic attraction. To limit the number of handling steps, the target nucleic acid may be amplified by simply mixing the target nucleic acid in the complex on the support with amplification oligomers and proceeding with amplification steps.

Amplifying a region of a target nucleic acid utilizes an in vitro amplification reaction using at least two amplification oligomers that flank a target region to be amplified. Suitable amplification methods include, for example, replicase-mediated amplification; polymerase chain reaction (PCR), including reverse transcription polymerase chain reaction (RT-PCR); ligase chain reaction (LCR); strand-displacement amplification (SDA); and transcription-mediated or transcription-associated amplification (TMA). Such amplification methods are well-known in the art and are readily used in accordance with the methods of the present invention.

Once one or more target regions are amplified to produce one or more corresponding amplification products, the amplification product(s) may be used in subsequent procedures deep sequencing, alignment, and analysis to detect a minority genotype for the target nucleic acid as described herein.

In certain embodiments, the target nucleic acid to be sequenced and analyzed according the present method is from a sample obtained from a patient suffering or at risk of a disease or disorder. In some such variations, the target nucleic acid is a disease-associated nucleic acid that may be characterized by heterogeneity within a single patient. Examples of such intra-patient heterogeneity include, e.g., intra-tumor genetic heterogeneity associated with some cancers as well as infectious agents (for example, hepatitis C virus (HCV)) that exhibit genetic heterogeneity within an infected subject due to, e.g., rapid mutation as it replicates. The methods of the present invention can be used to examine quasispecies complexity in such a patient and to detect a minority genotype that, for example, may be present in a low copy number during an early stage of infection or disease progression but that may be more resistant to treatment. In certain embodiments, where a detected minority genotype has a known effect on or correlation to efficacy and/or resistance to one or more treatment regimes for the disease or disorder, the method further includes determining a treatment regime for the patient based on the detected minority genotype. In some such embodiments, the method further includes administering the selected treatment regime to the patient.

The method of the present invention also has particularly useful applications in studying disease-associated nucleic acid complexity in a patient population. For example, in some embodiments, the minority genotype is detected in a plurality of samples from patients suffering from a disease or disorder, such as, e.g., an infectious disease (e.g., HCV infection) or a cancer. In more specific variations, the method can be used to examine genetic heterogeneity associated with disease subtypes in patient populations receiving one or more treatment regimes in order to more effectively interpret clinical testing data. For example, in some embodiments in which the minority genotype is detected in a plurality of samples from patients suffering from a disease or disorder, the patients are receiving a predetermined treatment regime for the disease or disorder. In some such variations, the method further includes (i) monitoring the patients to obtain efficacy and/or resistance data for the treatment regime and (ii) determining the presence or absence of a correlation between the detected minority genotype and the efficacy and/or resistance data. These variations are particularly useful for assessing drugs in order to more effectively stratify and interpret efficacy and resistance data.

For example, in some embodiments, a target nucleic acid is obtained from a plurality of samples from each of one or more patients suffering from a disease or disorder and receiving a treatment regime, where at least two of the samples from each patient each corresponds to a different time point during the course of treatment, and steps (a)-(d) as described herein are performed with respect to the target nucleic acid from each of the at least two samples. Typically, the method further includes a step in which, for each of one or more variants within the common set of significant variants determined in step (d), variant frequencies and/or variant significance values (e.g., Poisson p-values) for the samples corresponding to different time points are compared to determine whether the variant is a "differential variant" exhibiting different frequencies and/or significance values during the course of the treatment regime. If more than one minority genotype is detected within the samples corresponding to different time points, a subset of the minority genotypes may be selected and, for each of one or more variants within the common set of significant variants determined in step (d) for each of the detected minority genotypes or subset thereof, the variant frequencies and/or variant significance values for the samples corresponding to different time points may be compared to determine whether the variant is a differential variant. If a more than one differential variant is identified, a subset of the identified differential variants may be selected, and two-way hierarchical clustering may be performed on (1) the frequencies and/or significance values of the identified differential variants or subset thereof and (2) the samples containing the target nucleic acid in which differential variants were detected. Results from the two-way hierarchical clustering may then be used to determine a correlation between at least one differential variant and the course of the treatment regime. In some embodiments, the method further includes monitoring the one or more patients to obtain efficacy and/or resistance data for the treatment regime (typically including the same time points corresponding to the patient samples), and determining a correlation between at least one differential variant and the efficacy and/or resistance data (e.g., a correlation with at least one efficacy and/or resistance response to the treatment regime). Determining the presence of a correlation with efficacy and/or resistance data may include a comparison of the efficacy and/or resistance data with results from the two-way hierarchical clustering of differential variants across clinical samples. In particular embodiments, a differential variant is identified as one that is either resistant or susceptible to the treatment regime.

In other embodiments, a method of the present invention is used to examine genetic heterogeneity during the progression of a disease or disorder. In some such embodiments, the method includes obtaining a target nucleic acid from a plurality of samples from each of one or more patients suffering from the disease or disorder, where at least two of the samples from each patient each corresponds to a different time point during the course of the disease or disorder progression, and steps (a)-(d) as described herein are performed with respect to the target nucleic acid from each of the at least two samples. Typically, the one or more patients are also monitored for one or more symptoms of the disease or disorder at each of the different time points. In preferred embodiments, the variation detection results of step (b) include a determination of the frequency for each variant and/or the variant significance results of step (c) include a significance value (e.g., a Poisson p-value) assigned to each variant, and the method further includes a step in which, for each of one or more variants within the common set of significant variants determined in step (d), the variant frequencies and/or variant significance values for the samples corresponding to different time points are compared to determine whether the variant is a "differential variant" exhibiting different frequencies and/or significance values during the progression of the disease or disorder. If more than one minority genotype is detected within the samples corresponding to different time points, a subset of the minority genotypes may be selected and, for each of one or more variants within the common set of significant variants determined in step (d) for each of the detected minority genotypes or subset thereof, the variant frequencies and/or variant significance values for the samples corresponding to different time points may be compared to determine whether the variant is a differential variant. A correlation between at least one differential variant and the disease or disorder progression may also be determined. If a more than one differential variant is identified, a subset of the identified differential variants may be selected, and two-way hierarchical clustering may be performed on (1) the frequencies and/or significance values of the identified differential variants or subset thereof and (2) the samples containing the target nucleic acid in which differential variants were detected. Results from the two-way hierarchical clustering may then be used to determine a correlation between at least one differential variant and the disease or disorder progression.

The invention is further illustrated by the following non-limiting examples.

Example 1

A specific example of HCV quasi-species detection was performed to illustrate the practical applicability of the present invention. A deep sequencing assay was developed for deep sequencing of entire NS3, NS4 and NS5 regions from HCV by combining a hybridization-based Target Capture method, RT-PCR and Pacific Biosciences' single molecule real-time sequencing platform. This assay, together with associated bioinformatics data analysis, provides a method for investigating quasispecies complexity of HCV virus.

Table 1 below summarizes a specific experiment for which the variant analysis and clustering for linkage was performed. Sequencing data was generated from such a sequencing run. A specific set of steps are described that processed data generated from such a sequencing run.

TABLE 1

| Step | Summary |
|---|---|
| Target Capture | Gen-Probe's Hybridization based Target Capture of HCV RNA from serum/plasma. |
| Mutations | Two point mutations in NS3 were introduced into a cloned HCV 1a wild-type sequence. This mutated species is used as the minority species. |
| Amplicons | Reverse transcription PCR (RT-PCR) of selected viral regions. Wild-type and mutant species amplified separately. 1 kb amplicons of NS3 regions generated. |
| Sanger Sequencing | Amplicons of the mutated species resulting from the above step Sanger sequenced for confirmation. |
| Mixture | Wild-type and mutant species mixed in desired concentration e.g. 5% minority mutant species and 95% wild-type species. |
| Template preparation | Standard SMRTbell template preparation recommended for 1 kb amplicons using C2 chemistry kits. |
| Sequencing | Standard SMRT Sequencing on 8 or 16 SMRTcells using C2 chemistry and compatible instrument software. |

1) Sequence Alignment

All circular consensus sequences (CCS) produced by the PacBio RS for a given SMRTcell were mapped to the reference sequence with BWA-SW, using the parameters recommended by the Broad Institute for mapping PacBio data. All sequencing reads that did not form CCS were discarded. All CCS reads that did not map to the reference were discarded. For CCS reads with multiple mappings, only the alignment with the highest overall mapping quality was retained. The resulting file was a SAM formatted file. This corresponds to step 200 in FIG. 1.

Error analysis of alignment was performed. At each base position, if the sequence nucleotide did not match the reference nucleotide, the base position was marked erroneous. Error rate at a particular base position was defined by a ratio where the numerator is number of errors across all sequences at the particular base position and denominator is the number of sequences that span the base position.

The raw sequencing reads from PacBio RS can also be aligned to generate SAM file and all subsequent steps are applicable. But the error rate of raw reads is significantly higher than CCS reads and may not result in usable data when the variant frequency is low (e.g., <20%).

2a) Variant Identification—Nucleotide Space

All aligned CCS reads were piled-up on a nucleotide-by-nucleotide basis in a manner identical to the samtools pileup format. This created, for each nucleotide in the reference sequence, a list of all nucleotides aligned to that position from the alignments retained above. This list of aligned sub-sequences was then filtered to remove insertions and deletions, and to remove all sub-sequences below a quality threshold. At any reference position, the list of variants was gathered. If the reference at position p is an A, and if there are 100 sequences that are aligned at position p and 50 of them are A, 45 are T, 5 are C, then the possible variants at position p are {T, C}. This step corresponds to step 300 in the FIG. 1.

Once the variants were identified, their p-values were computed. From the error analysis, the "baseline" substitution error at mean read length was chosen. Then at a given position, the frequency for a given variant was observed. The likelihood for this variant at this position was computed as L=−2*Ln(baseline substitution error rate/observed frequency)=2*Ln(observed frequency/baseline substitution error rate). The p-value was computed assuming degree of freedom=1 and Chi-square distribution, as shown below:

1. For each variant type at each position, calculate the log-likelihood ratio of variant frequency vs. positional substitution error, $$L = 2*\text{Ln}\left(\frac{freq(\text{Observed Variant})}{freq(\text{Underline Substitution Errors})}\right)$$

2. L is subject to Chi-squared distribution with degree of freedom=1.
3. The cumulative Chi-squared distribution formula (usually Chi-squared CDF is available from most of scientific softwares, including MS Excel).

$$P \text{ value} = 1 - CDF\chi^2(L, k) = 1 - \frac{\gamma\left(\frac{k}{2}, \frac{L}{2}\right)}{\Gamma\left(\frac{k}{2}\right)}$$

When the degree of freedom k=1, $$P \text{ value} = 1 - \frac{1}{\sqrt{\pi}} * \sqrt{\pi} \text{ erf}\left(\sqrt{\frac{L}{2}}\right)$$

$$= 1 - \text{erf}\left(\sqrt{\frac{L}{2}}\right)$$

Where the error function, erf, is defined as, $$\text{erf}(z) = \frac{2}{\sqrt{\pi}} \sum_{n=0}^{\infty} \frac{(-1)^n z^{2n+1}}{n!(2n+1)} = \frac{2}{\sqrt{\pi}}\left(z - \frac{z^3}{3} + \frac{z^5}{10} - \frac{z^7}{42} + \frac{z^9}{216} - \cdots\right)$$

Example:
Without loose generality, the "baseline" substitution error is chosen at mean read length. In this case, 0.11% is used as the baseline substitution error. If at a given position, the observed frequency rate for a given variant is 0.98%, the likelihood for this variant at the position is $$L=2*Ln(0.98/0.11)=4.374$$

With degree of freedom=1, we can calculate the p value of L=4.374 based on Chi-squared distribution p=0.03649124.

The lower the p-value is, the more significant the variant is. Typically at each site, one of the variant will emerge as the most significant variant at that particular position. The results of all of the significance tests from all of the analyzed positions were then combined into a list and sorted by p-value. Table 2 describes the resulting most significant variants. This analysis of significance corresponds to step 400 in the overview.

TABLE 2

Top 10 Variants

| Rank Order | Reference Position | Depth | Top Variant Frequency % | P Value | Reference Seq | Top Variant |
|---|---|---|---|---|---|---|
| 1 | 446 | 1739 | 4.95 | 0.0085 | C | T |
| 2 | 482 | 1740 | 4.83 | 0.0087 | A | T |
| 3 | 414 | 1737 | 0.98 | 0.0548 | C | G |
| 4 | 154 | 1724 | 0.70 | 0.0829 | G | C |
| 5 | 973 | 1725 | 0.64 | 0.0924 | C | G |
| 6 | 922 | 1726 | 0.64 | 0.0925 | G | C |
| 7 | 350 | 1735 | 0.63 | 0.0931 | G | C |
| 8 | 28 | 1705 | 0.53 | 0.1173 | A | G |
| 9 | 239 | 1731 | 0.52 | 0.1195 | C | G |
| 10 | 151 | 1723 | 0.46 | 0.1383 | G | C |

2b) Variant Identification—Codon Space

All aligned CCS reads were piled-up on a codon-by-codon basis in a manner similar to the samtools pileup format. This created, for each codon in the reference sequence, a list of all codons aligned to that position from the alignments retained above. This list of aligned sub-sequences was then filtered to remove insertions and deletions, and to remove all sub-sequences below a quality threshold. The coverage at a given position is defined as the number of sub-sequences remaining aligned to that position after this filtering has been performed. If the codon at position p is GCC and the coverage is 100, and 50 of them are GCC, 45 are GTC, 5 are GGC, then the possible variants at position p are {GTC, GGC}. This step corresponds to step 300 in FIG. 1.

Next, the counts for each of the variant codons were identified from the pileup and tabulated. Laplacian smoothing was then applied to resulting counts. Each smoothed variant count was then compared to its expected value, which was estimated as the coverage at a given position multiplied by the rate of similar mutations observed in a large corpus of control data. The significance of the difference between these two numbers was estimated with a one-tailed test from the Poisson distribution. The observed p-values can also be corrected using Bonferroni correction to mitigate false discovery rate. The lower the p-value is, the more significant the variant is. The results of all of the significance tests from all of the analyzed positions were then combined into a list and sorted by p-value. Table 3 describes the resulting most significant variants. This analysis of significance corresponds to step 400 in FIG. 1.

TABLE 3

Top 10 Mutants Frequencies

| Reference Position | Reference Codon | Mutant Codon | Frequency % | Pvalue |
|---|---|---|---|---|
| 161 | GAC | GTC | 1.18 | 9.095E−31 |
| 149 | GCC | GTC | 0.97 | 9.049E−18 |
| 138 | TGC | TGG | 0.90 | 1.604E−09 |
| 270 | GGT | GGC | 0.50 | 9.917E−06 |
| 139 | CCC | CCG | 0.35 | 2.105E−05 |
| 307 | GGG | GTG | 0.36 | 6.687E−05 |
| 19 | AAA | TAA | 0.15 | 7.150E−05 |
| 107 | ATT | GTG | 0.07 | 1.172E−04 |
| 321 | TCC | ACC | 0.14 | 2.029E−04 |
| 247 | ACC | ACG | 0.21 | 2.688E−04 |

3) Data Preparation for Clustering

A subset of the most significant variants from the list generated above were then selected for linkage analysis. Either the top 25 variants or all variants with p-values <0.001 was selected, depending on which criteria was more stringent.

Returning to the aligned CCS reads, a matrix of presence-absence calls was generated for the selected variants in each of the alignments with one column for each variant in the subset and one row for each aligned sequence. Each read was then iterated over and each position with at least one variant from the selected subset was examined. The presence of such a mutation was recorded as a '1' in the appropriate position in the data matrix, while its absence was recorded as a '0.' Any such positions that were un-readable due to deletions or clipping of low-quality sequence were assumed to be wild-type and recorded as a '0' to minimize the chance of false-positives. Finally, a small amount of random noise was added to every cell in the matrix to ensure the final data matrix was invertible and non-degenerate.

4) NMF Clustering

The first step to performing any clustering analysis is to estimate the optimal number of clusters or rank in the result. To do this, the NMF algorithm (see, e.g., Gaujoux R, Seoighe C., *BMC Bioinformatics* 11:367, 2010) was run 10 times at each value in a range of possible ranks, typically from 2 to 15. For each rank, only the most accurate result was retained as determined by which replication had the lowest residual sum-of-squares at the termination of the algorithm. Next, the cophenetic correlation was calculated for the best matrix from each rank to estimate the goodness-of-fit of each set of clusters. The results were then graphed and inspected, and the first rank that showed a decrease in cophenetic correlation relative to the preceding position (i.e., the first rank that begins to show over-training) was selected as the optimal rank.

Once the optimal rank was selected, the NMF algorithm was re-run an additional 100 times on the data set with the selected rank. The most accurate result as determined by the residual sum-of-squares was then retained for detailed analysis.

The primary output of the clustering analysis was a matrix of dimensions R-by-N, where R was the selected rank and N was the size of the variant subset. The numbers in the matrix thus corresponded to the raw weight assigned to a given variant in a particular cluster, so to accurately separate the major and minor components of each cluster a copy of the matrix was made and normalized such that the contents of each row (cluster) to sum to 1. From this normalized matrix the major variants of each cluster were identified as those components with normalized weightings above a threshold (usually 0.1). Any remaining non-zero components likely corresponded to sequencing errors; therefore, the corresponding values in the un-normalized matrix were set to '0' so they did not affect the scoring of the clusters.

The secondary output of the clustering analysis was a matrix of basis values of dimensions M-by-R, where M was the number of reads in the original matrix and R was the rank selected. The values of each row in this matrix corresponded to the weight of each of the R clusters needed to approximate the corresponding row from the original matrix. Therefore, to score each of the clusters, the original matrix from each cluster was recomposed individually and its similarity to the original data matrix was measured. To do so, each column of basis values from this M-by-R matrix and the corresponding row from the matrix of cluster weightings were selected and then multiplied to get X', an estimation of the original matrix X. This estimate was then subtracted from the original matrix X to get a difference matrix, D. The score for the cluster can then be calculated as the difference between the sum-of-squares of these matrices, respectively $X_{SS}$ and $D_{SS}$. This difference, the explained sum-of-squares or $E_{SS}$, represented the amount of information from matrix X captured in the estimation X' generated from a given cluster. Finally, in order to present the results in a normalized and human-readable format, the ratio of the explained sum-of-squares was used to the total ($E_{SS}/X_{SS}$). This step corresponds to step 500 in the FIG. 1.

5) Human Readable Data Output

Clusters were sorted in descending order of the explained sum-of-squares, and output with the names of the columns making significant contributions to that cluster, i.e., the variants that are a part of a given linkage grouping. Also output were the inclusive and exclusive counts for each cluster, which were the number of reads exhibiting at least one of the variants in a cluster, and the number of reads exhibiting all of them, respectively. Table 4 describes a sample output from the analysis. In this particular case, the minority species with two relevant mutations were seen as the most significant cluster.

samples using a method similar to that outlined in parts 1 through 5 of Example 1. Briefly, circular consensus sequences (CCS) produced by the PacBio RS for a given SMRTcell were aligned to the consensus sequence of HCV with BWA-SW. BWA-SW parameters used in this study included the following: mismatch penalty—3; gap open penalty—5; gap extension penalty—2; more penalty for indels; less penalty for mismatches. Codons exhibited in the CCS reads were piled-up along the reference based on the first reading frame. Variant codons in the samples were detected compared to the reference sequence, and the frequency of each variant was calculated. A Lambda table was created based on the codon pile up of wild-type (or control) sample. A Poisson distribution of variants was assumed and the P value for each detected variant was calculated using the Lambda table.

For NMF clustering, about half of the reads were filtered out based on base quality score, and variant codons with <1% frequency were removed (p-values could also be used as a basis for removing variants). An assumption of 10 clusters was used: 10 clusters of variant codons were obtained from each run, with about 200 variant codons per run.

The top-scoring NMF clusters were then compared between clinical samples corresponding to the −1T, 1T, 2T, and 4T time points to identify clusters exhibiting different frequencies during the course of antiviral drug treatment, thereby identifying clusters—and the variant codons contributing to each cluster—that relate to drug responses. Two-way hierarchical clustering was performed with the variant codons contributing to each cluster ("differential variants") and the clinical samples corresponding to the different time points to create a heat map of 119 differential variants plotted against the time-associated samples.

Based on the two-way hierarchical clustering, correlations between differential variants and the drug treatment time course were determined. Certain differential variants were found to fit within particular correlation profiles. With "+" indicating a higher frequency of the differential variant and

TABLE 4

| Cluster Score | Inclusive Count (% of TOTAL) | Exclusive Count (% of TOTAL) | Mutations with significant contribution to the cluster; Position (Reference > Mutant) |
|---|---|---|---|
| 25.67 | 18 (1.24%) | 13 (0.89%) | 149 (GCC > GTC), 161 (GAC > GTC) |
| 11.68 | 13 (0.89%) | 13 (0.89%) | 138(TGC > TGG) |
| 8.07 | 9 (0.62%) | 9 (0.62%) | 270(GGT > GGC) |
| 7.3 | 9 (0.62%) | 1 (0.07%) | 94(TCC > GCC), 139(CCC > CCG) |
| 6.4 | 7 (0.48%) | 1 (0.07%) | 215(GGC > GGFA), 256(AGC > AGG) |
| 5.4 | 6 (0.41%) | 6 (0.41%) | 307(GGG > GTG) |
| 2.4 | 15 (1.03%) | 0 (0.00%) | 18(GAC > AAC), 57(ATC > ACC), 123 (CGG, GGG) |

Example 2

The deep sequencing assay referenced in Example 1—for deep sequencing of the entire NS3, NS4 and NS5 regions from HCV by combining a hybridization-based Target Capture method, RT-PCR and Pacific Biosciences' single molecule real-time sequencing platform—was run on clinical samples from HCV-infected patients. The clinical samples were taken both before and after the start of antiviral drug treatment, at four different time points: one day before treatment started (−1T), one day after treatment started (1T), two days after treatment started (2T), and four days after treatment started (4T).

Variant analysis and NMF clustering for linkage was performed on the deep sequencing results from these "−" indicating a lower frequency for times (−1T/1T/2T/4T), five such profiles were defined as follows: (+/+/+/−) for Profile 1; (−/−/+/−) for Profile 2; (+/+/−/+) for Profile 3; (−/+/++/+++) for Profile 4; and (+/−/−/+) for Profile 5.

Sanger sequencing was also performed to confirm the identified differential variants. Results showed that 86% of the differential codon variants as determined by Sanger sequencing were detected by NMF clustering, while 83% of the differential codon variants as determined by Sanger sequencing were detected by the heat map profile filtering method described above.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A method for detecting a minority genotype of a target nucleic acid of a virus in a population of patients undergoing a population treatment regime, the treatment regime comprising receiving a drug for treating an infection by the virus, the patients being monitored to provide resistance data of the drug, the method comprising:
   (a) deep sequencing at least a portion of the target nucleic acid, wherein the deep sequencing is selected from the group consisting of: single molecule real time sequencing, ion semi-conductor sequencing, and bridge polymerase chain reaction sequencing,
   (b) detecting, using the deep sequencing results of (a), a presence of variant nucleobases at one or more nucleotide reference positions within the target nucleic acid;
   (c) calculating p-values of the variants detected in step (b) and selecting statistically significant variants with the lowest p-values or for which the p-values are below a threshold;
   (d) clustering, using non-negative matrix factorization, the statistically significant variants of step (c) into clusters;
   (e) correlating the clusters of statistically significant variants with the drug resistance data;
   (f) determining a patient treatment regime, different than the population treatment regime, for a patient infected with the virus and having received the drug, from the population of patients or otherwise, based on a determined presence in the patient of a cluster of statistically significant variants correlated with drug resistance in the population as determined in step (e), wherein the patient treatment regime is tailored to the drug resistance; and
   (g) administering the determined patient treatment regime to the patient; wherein the virus is hepatitis C and the patient treatment regime and the population treatment regime is each from a class of drugs selected from NS3/4A protease inhibitors, non-nucleoside inhibitors of RdRp and NS5A inhibitors, the selected classes being different for the patient treatment regime and the population treatment regime.

2. The method of claim 1, wherein said variant detection and variant significance is based on a log likelihood-ratio model for nucleotide variant detection, or a Poisson distribution model for codon variant detection.

3. The method of claim 1, wherein said variant detection and variant significance is based on a Bayesian model.

4. The method of claim 1, wherein the statistically significant variants determined in step (c) are subjected to smoothing or a derivative thereof before proceeding to step (d).

5. The method of claim 1, wherein the statistically significant variants determined in step (c) are subjected to correction by a false discovery rate minimization method before proceeding to step (d).

6. The method of claim 5, wherein the false discovery rate minimization method includes Bonferroni correction or a derivative thereof.

7. The method of claim 5, wherein the false discovery rate minimization method includes Benjamini and Hochberg correction or a derivative thereof.

8. The method of claim 1, further comprising amplifying one or more regions of the target nucleic acid prior to step (a), and wherein said deep sequencing comprises sequencing the one or more amplified regions.

9. The method of claim 1, wherein the target nucleic acid comprises at least one of the NS3, NS4, and NS5 regions from HCV.

10. The method of claim 1,
   wherein at least two samples are collected from each patient in the population, wherein each sample of the at least two samples corresponds to a different time point during a course of the population treatment regime, wherein steps (a)-(d) are performed with respect to the target nucleic acid from each of the at least two samples, and
   (i) wherein the variant detection results of step (b) include a determination of the frequency for each variant and/or the variant significance results of step (c) include a significance value assigned to each variant, and wherein the method further comprises
      (h) for each of one or more variants within the common set of significant variants determined in step (d), comparing the variant frequencies and/or variant significance values for the samples corresponding to different time points to determine whether the variant is a differential variant exhibiting different frequencies and/or significance values during the course of the treatment regime; or
   (ii) wherein a plurality of minority genotypes are detected within the samples corresponding to different time points, wherein the variant detection results of step (b) include a determination of the frequency for each variant and/or the variant significance results of step (c) include a significance value assigned to each variant, and wherein the method further comprises
      (i) optionally selecting a subset of the plurality of minority genotypes; and
      (j) for each of one or more variants within the common set of significant variants determined in step (d) for each minority genotype within said plurality or optional subset thereof, comparing the variant frequencies and/or variant significance values for the samples corresponding to different time points to determine whether the variant is a differential variant exhibiting different frequencies and/or significance values during the course of the treatment regime.

11. The method of claim 10, wherein a plurality of differential variants are identified in step (j), and wherein the method further comprises
   (k) selecting at least a subset of the plurality of differential variants; and
   (l) performing two-way hierarchical clustering on (1) the frequencies and/or significance values of the differential variants within said plurality or subset thereof and (2) the samples containing the target nucleic acid in which said differential variants were detected, each sample corresponding to a time point.

12. The method of claim 10, further comprising confirming at least one differential variant by Sanger sequencing.

* * * * *